United States Patent
Chen et al.

(10) Patent No.: US 10,631,576 B1
(45) Date of Patent: Apr. 28, 2020

(54) ATOMIZING DEVICE AND ELECTRONIC CIGARETTE HAVING THE SAME

(71) Applicant: SMISS TECHNOLOGY CO., LTD., Shenzhen (CN)

(72) Inventors: Jiatai Chen, Shenzhen (CN); Chengzhi Zhao, Shenzhen (CN); Shuiming Deng, Shenzhen (CN); Ningbo Qiu, Shenzhen (CN); Ming Chen, Shenzhen (CN); Wanxiang Zou, Shenzhen (CN)

(73) Assignee: SMISS TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/423,285

(22) Filed: May 28, 2019

(30) Foreign Application Priority Data

Apr. 4, 2019 (CN) .......................... 2019 1 0272304

(51) Int. Cl.
*A24F 47/00* (2020.01)
*A24F 40/42* (2020.01)
*A61M 15/06* (2006.01)

(52) U.S. Cl.
CPC ............ *A24F 47/008* (2013.01); *A24F 40/42* (2020.01); *A61M 15/06* (2013.01)

(58) Field of Classification Search
CPC ............................. A24F 47/008; A61M 15/06
USPC ......................................................... 131/330
See application file for complete search history.

(56) References Cited

U.S. PATENT DOCUMENTS

| | | | |
|---|---|---|---|
| 9,549,573 B2 * | 1/2017 | Monsees | H05B 3/04 |
| 2014/0130817 A1 * | 5/2014 | Li | A24F 47/008 |
| | | | 131/329 |
| 2015/0173420 A1 * | 6/2015 | Shi | A24F 47/008 |
| | | | 131/329 |
| 2016/0219939 A1 * | 8/2016 | Li | A24F 47/008 |
| 2017/0208863 A1 * | 7/2017 | Davis | A24F 47/008 |
| 2018/0243520 A1 * | 8/2018 | Johnson | A61M 15/06 |
| 2019/0350263 A1 * | 11/2019 | Qiu | A24F 47/00 |

FOREIGN PATENT DOCUMENTS

| | | | | |
|---|---|---|---|---|
| CN | 207855027 U | * | 9/2018 | ........... A24F 47/008 |
| CN | 207940346 U | | 10/2018 | |
| KR | 20180038630 A | | 4/2018 | |
| WO | 2018000367 A1 | | 1/2018 | |
| WO | 2018133267 A1 | | 7/2018 | |

OTHER PUBLICATIONS

Machine Translation CN 207588027 U (Year: 2018).*
European Search Report for European Counterpart Application No. 19177254.0, dated Jan. 16, 2020 (12 pages).

* cited by examiner

*Primary Examiner* — Eric Yaary
*Assistant Examiner* — Russell E Sparks
(74) *Attorney, Agent, or Firm* — Kagan Binder, PLLC (57) ABSTRACT

The present disclosure relates to an atomizing device and an electronic cigarette provided with the atomizing device. The atomizing device includes a liquid storage housing and a sealing plug, and the liquid storage housing is provided with a liquid storage chamber and a liquid injection channel connecting the liquid storage chamber and the external environment. The sealing plug is detachably inserted into the liquid injection channel to open or seal the liquid storage chamber. An end of the sealing plug away from the liquid storage chamber forms a magnetic attraction surface with magnetism.

13 Claims, 6 Drawing Sheets

ATOMIZING DEVICE AND ELECTRONIC CIGARETTE HAVING THE SAME

CROSS-REFERENCE TO RELATED APPLICATION

This application claims the benefit of Chinese Patent Application No. 2019102723046, filed on Apr. 4, 2019, the entire content of which is incorporated herein in its entirety.

TECHNICAL FIELD

The disclosure relates to cigarette substitute products, and more particular to an atomizing device and an electronic cigarette having the same.

BACKGROUND

Smoking has become the biggest preventable cause of death in the world due to the presence of nicotine, tar and other harmful substances in the smoke produced by tobacco burning, and the exposure of second-hand smoke of people around smokers can also cause harm to the body. Therefore, with the progress of science and technology and increasing attention to health, the use of electronic cigarette is more and more widespread. Most electronic cigarette can produce smoke by atomization of the atomizing liquid, which effectively reduces the generation of harmful substances compared with the direct combustion of cut tobacco, and which reduces the harm to smokers and the people around them to some extent.

The atomizing device, as the core structure of the electronic cigarette, mainly includes a liquid storage chamber, an atomizing core, a liquid storage medium and a heating body, and so on. The atomizing liquid in the liquid storage chamber is introduced into the liquid storage medium through the liquid inlet hole on the atomizing core. The heating element serves as a heating element for heating the atomizing liquid in the liquid storage medium. When power is supplied to the heating body, the heating body heats up the atomizing liquid in the liquid storage medium, thereby realizing atomization of the atomizing liquid and generating smoke.

At present, the assembly mode of the atomizing device and the power supply device for supplying power to the heating body is usually a latching fit, however, the mutually engaged snaps may be worn after a long time contact, resulting in poor contact between the atomizer and the power supply device, such that the service life of the electronic cigarette is shortened.

SUMMARY

According to various embodiments of present disclosure, an atomizing device and an electronic cigarette having the atomizing device are provided.

An atomizing device includes a liquid storage housing and a sealing plug. The liquid storage housing is provided with a liquid storage chamber and a liquid injection channel communicating the liquid storage chamber with an external environment, and the sealing plug is detachably inserted into the liquid injection channel to open or seal the liquid storage chamber. An end of the sealing plug away from the liquid storage chamber is provided with a magnetic attraction surface having magnetism.

An electronic cigarette includes a liquid storage housing and a sealing plug. The liquid storage housing is provided with a liquid storage chamber and a liquid injection channel communicating the liquid storage chamber with an external environment and the sealing plug is detachably inserted into the liquid injection channel to open or seal the liquid storage chamber. An end of the sealing plug away from the liquid storage chamber is provided with a magnetic attraction surface having magnetism. The atomizing device has a power supply device provided with a magnetic element. The magnetic element and the magnetic attraction surface are connected to each other under a magnetic attraction, such that the atomizing device is coupled to the power supply device.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

Embodiments of the present disclosure are described more fully hereinafter with reference to the accompanying drawings. The various embodiments of the present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art.

It will be understood that when an element is referred to as being "fixed" to the other element, it can be directly fixed to the other element or intervening elements may be present. Also, when an element is referred to as being "connected" or "coupled" to the other element, it can be directly connected or coupled to the other element or intervening elements may be present. As used herein, the terms "vertical", "horizontal", "left", "right" and the like are merely for the illustrative purpose.

Unless otherwise defined, all technical and scientific terms used herein have the same meaning as commonly understood by those persons skilled in the art to which this disclosure belongs. The terms used in the description of the present disclosure are only for the purpose for describing specific embodiments, and could not limit the present disclosure. The term "and/or" used herein should include any one of and all of the combinations of one or more relevant listed items.

Figure 1:
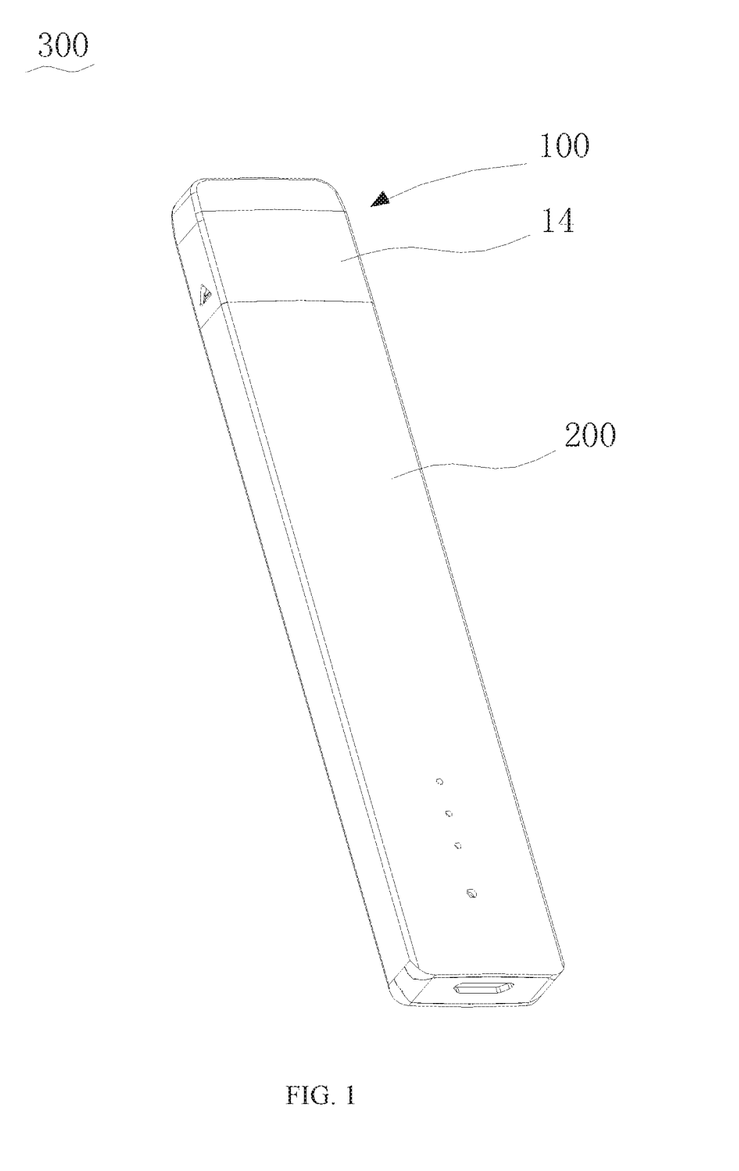
FIG. 1 is a perspective view of an electronic cigarette according to an embodiment.
Figure 2:
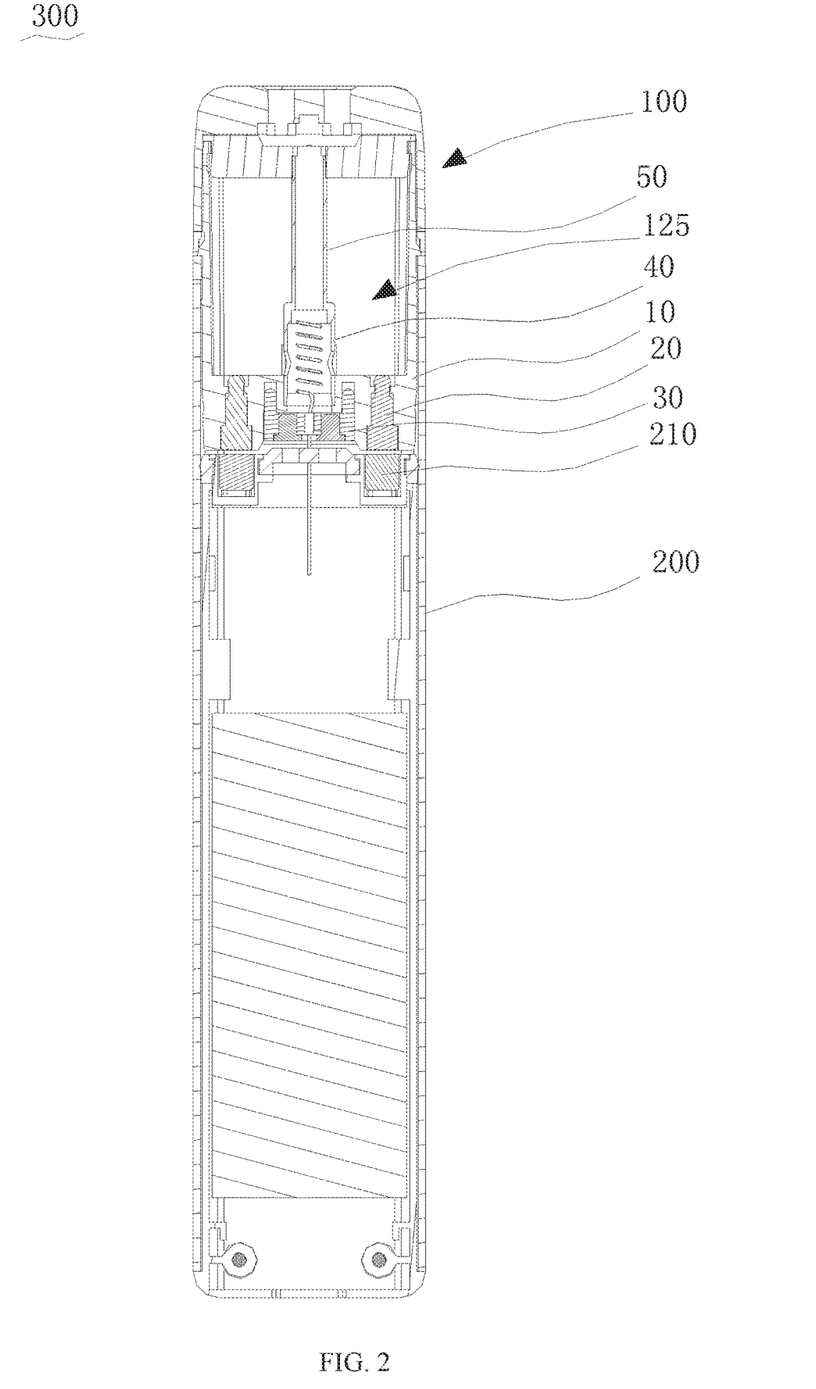
FIG. 2 is a cross-sectional view of the electronic cigarette of FIG. 1.

As shown in FIG. 1 and FIG. 2, an electronic cigarette 300 according to an embodiment includes a power supply device 200 and an atomizing device 100 coupled to one end of the power supply device 200. The power supply device 200 is used to supply power to the atomizing device 100. The atomizing device 100 is used to store the atomizing liquid and heat the atomizing liquid tinder the electric driving of the power supply device 200 to atomize the atomizing liquid to form a smoke for the user to suck. The specific structure of the power supply device 200 is basically the same as the structure of the power supply device in the prior art, so it is not described in detail here.

Figure 3:
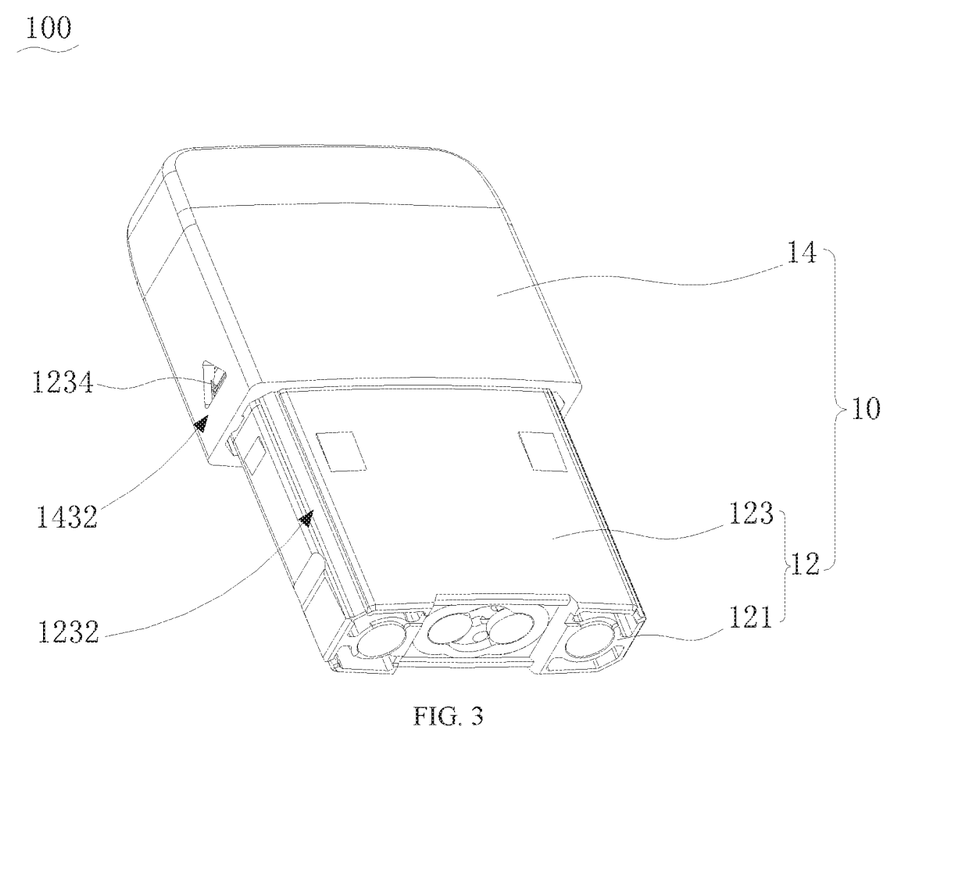
FIG. 3 is a perspective view of an atomizing device of the electronic cigarette of FIG. 1.

As shown in FIG. 1 to FIG. 3, the atomizing device 100 includes a liquid storage housing 10, an atomizing core 40 accommodated in the liquid storage housing 10, a vent tube 50 accommodated in the liquid storage housing 10, and an atomizing base 30 fixed under the liquid storage housing 10. A liquid storage chamber 125 for storing the atomizing liquid is formed in the liquid storage housing 10, and the atomizing core 40 is used to absorb the atomizing liquid in the liquid storage chamber 125, and the atomizing base 30 is used to electrically couple the atomizing core 40 to the power supply device 200. The smoke generated by atomizing the atomizing liquid in the energized atomizing core 40 flows into the vent tube 50 and is finally inhaled by the user.

Figure 4:
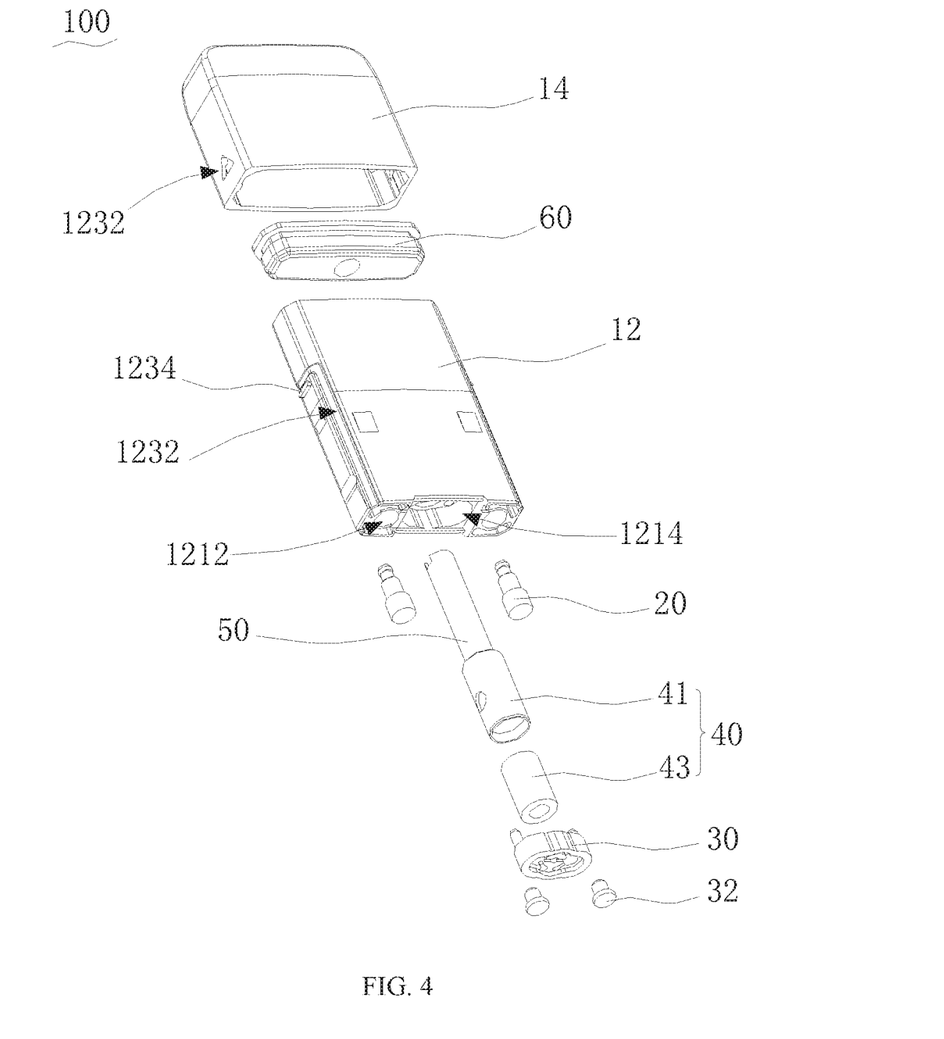
FIG. 4 is an exploded view of the atomizing device of FIG. 3.
Figure 5:
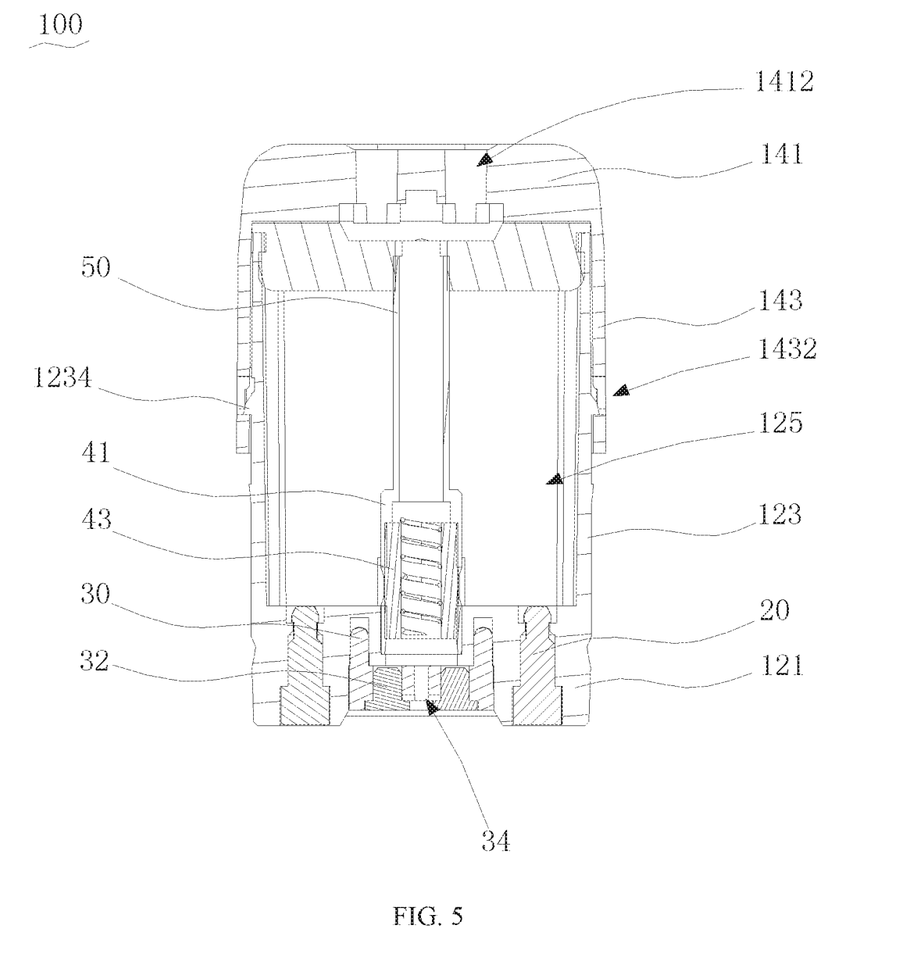
FIG. 5 is a cross-sectional view of the atomizing device of FIG. 3.
Figure 6:
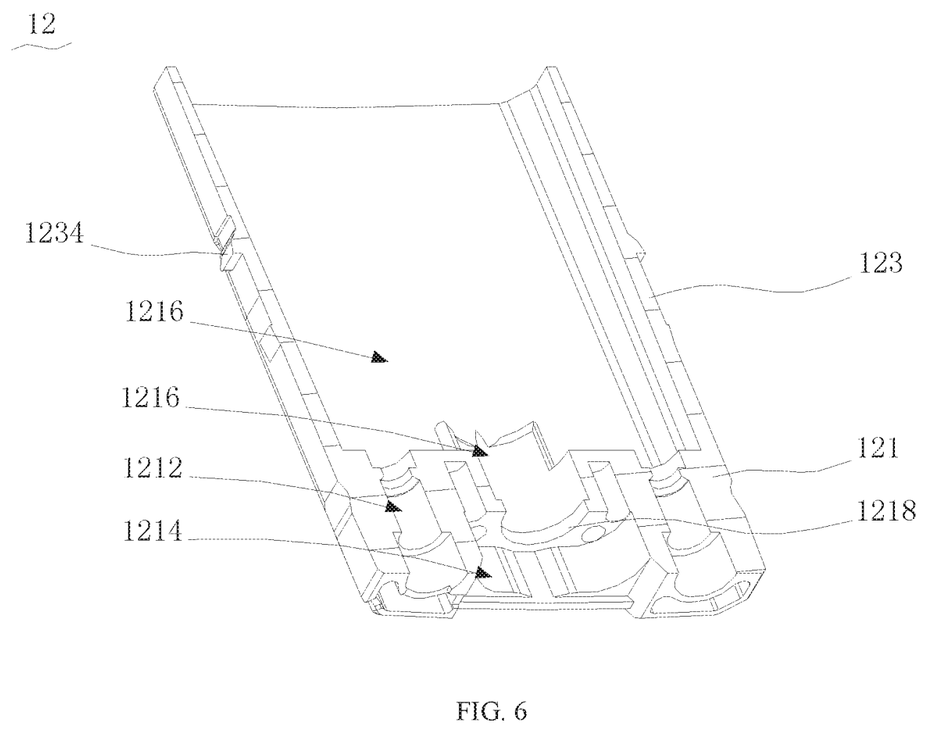
FIG. 6 is a cut away view of a liquid storage cartridge of the atomizing device of FIG. 3.

Referring to FIG. 4 to FIG. 6, the liquid storage housing 10 includes a liquid storage cartridge 12 and a nozzle cover 14 detachably sleeved on one end of the liquid storage cartridge 12, and the end of the liquid storage cartridge 12 not covered with the nozzle cover 14 is inserted into the power supply device 200.

In particular, the liquid storage cartridge 12 includes a liquid storage bottom wall 121 and a liquid storage side wall 123 extending in the same direction from an edge of the liquid storage bottom wall 121. The liquid storage side wall 123 surrounds the liquid storage bottom wall 121 and cooperatively forms the liquid storage chamber 125 with one end opening together with the liquid storage bottom wall 121.

The liquid storage bottom wall 121 is provided with a liquid injection channel 1212 through which the liquid storage chamber 125 communicates with the external environment. The sealing plug 20 is detachably inserted into the liquid injection channel 1212 to open or seal the liquid storage chamber 125. Thus, when the liquid injection channel 1212 is not provided with the sealing plug 20, the atomizing liquid may be injected into the liquid storage chamber 125 through the liquid injection channel 1212. After the sealing plug 20 is inserted into the liquid injection channel 1212 to seal the liquid storage chamber 125, the atomizing liquid cannot flow out of the liquid storage chamber 125 through the liquid injection channel 1212.

Particularly, in sonic of the embodiments, the liquid storage bottom wall 121 is longitudinally provided with two liquid injection channels 1212 spaced with each other, each of which is detachably mounted with a sealing plug 20. In this way, the atomizing device 100 injects the atomizing liquid by means of injection from the bottom. When the atomizing liquid is injected into the liquid storage chamber 125, the atomizing device 100 is in an inverted state, the two liquid injection channels 1212 can be opened simultaneously, and the user injects the atomizing liquid into the liquid storage chamber 125 through any one of the liquid injection channels 1212. During the injecting process, the air in the liquid storage chamber 125 is discharged through the other liquid injection channel 1212. Therefore, the injected atomizing liquid can fill the entire liquid storage chamber 125, thereby preventing negative pressure with the external air due to the air in the liquid storage chamber 125 being unable to be discharged, and finally preventing the atomizing liquid from flowing out of the liquid storage chamber 125 under the negative pressure. It should be understood that the number of the liquid injection channels 1212 is not limited thereto, and in alternative embodiments, the liquid storage bottom wall 121 may have a plurality of liquid injection channels 1212 spaced apart to improve the air discharge effect.

In some of the embodiments, the end of the sealing plug 20 away from the liquid storage chamber 125 forms a magnetic attraction surface with magnetism that is substantially flush with the surface of the liquid storage bottom wall 121 on the side thereof away from the liquid storage chamber 125. Referring to FIG. 2, a magnetic element 210 is disposed at one end of the power supply device 200 coupled to the atomizing device 100. The magnetic element 210 can be connected to the magnetic attraction surface of the sealing plug 20 of the atomizing device 100 by magnetic attraction such that the atomizing device 100 is coupled to the power supply device 200.

Particularly, in some of the embodiments, the sealing plug 20 is formed of a magnetic material capable of having magnetic attraction with a magnet, and the magnetic element 210 is formed of a magnet, thereby reducing the manufacturing cost of the electronic cigarette 300. It should be understood that in some of the embodiments, the sealing plug 20 is formed of a magnet and the magnetic element 210 is formed of a magnetic material that has magnetic attraction with the magnet. In some of the embodiments, the sealing plug 20 and the magnetic element 210 are formed of magnets of opposite polarities, respectively. In alternative embodiments, the sealing plug 20 and the magnetic element 210 may also be composed of other materials and magnets, so long as the sealing plug 20 and the magnetic element 210 can be absorbed to each other.

In this way, the atomizing device 100 and the power supply device 200 are connected to each other by magnetic attraction through the sealing plug 20, thereby replacing the conventional latching structure which is prone to failure due to wear, such that the atomizing device 100 and the power supply device 200 can be conveniently, quickly and stably connected for a long time. Moreover, since the sealing plug 20 integrates the function of sealing the liquid injection channel 1212 and the connection power supply device 200, there is no need to separately provide an extra structure in the atomizing device 100 in order to connect the power supply device 200. Thus, the structure of the atomizing device 100 is simplified, and the development of volume miniaturization of the atomizing device 100 and the electronic cigarette 300 is facilitated.

The liquid storage bottom wall 121 further has an atomizing base mounting slot 1214 for mounting the atomizing base 30 and an atomizing core mounting slot 1216 for mounting the atomizing core 40. In particular, that atomizing base mounting slot 1214 is at the side of the liquid storage bottom wall 121 away from the liquid storage chamber 125, and one end of the atomizing base mounting slot 1214 communicates with the external environment, the other end of the atomizing base mounting slot 1214 communicates with the atomizing core mounting slot 1216. The atomizing core mounting slot 1216 is provided at a side of the liquid storage bottom wall 121 adjacent to the liquid storage chamber 125, and one end of the atomizing core mounting slot 1216 communicates with the atomizing base mounting slot 1214, the other end of the atomizing core mounting slot 1216 communicates with the liquid storage chamber 125, and an annular resisting wall 1218 is formed between the atomizing base mounting slot 1214 and the atomizing core mounting slot 1216. Thus, the atomizing base 30 and the atomizing core 40 are limited in the atomizing base mounting slot 1214 and the atomizing core mounting slot 1216, respectively.

One end of the atomizing core 40 is inserted into the atomizing core mounting slot 1216 and resists the resisting wall 1218, and the other end of the atomizing core 40 is in the liquid storage chamber 125. The atomizing core 40 includes an atomizing core housing 41 and an atomizing core body 43. An atomizing chamber is formed in the atomizing core housing 41, and an atomizing hole communicating between atomizing chamber and the liquid storage chamber 125 is formed in a side wall of the atomizing core housing 41. The atomizing core body 43 is accommodated in the atomizing chamber of the atomizing core housing 41 and contacts the atomizing liquid in the liquid storage chamber 125 through the atomizing hole.

Thus, the atomizing core 40 accommodated in the atomizing chamber absorbs the atomizing liquid in the liquid storage chamber 125 through the atomizing hole, thereby atomizing the atomizing liquid to smoke. Since the atomizing core 40 is mounted on the liquid storage bottom wall 121 on the same side with the liquid injection channel 1212 in the liquid storage chamber 125, when the atomizing device 100 is inverted and the atomizing liquid is injected into the liquid storage chamber 125 through the liquid injection channel 1212, the atomizing liquid is located at the end of the liquid storage chamber 125 adjacent to the nozzle cover 14 due to gravity and is always isolated from the atomizing core 40, such that the atomizing liquid does not flow out of the liquid storage chamber 125 through the atomizing core 40.

The atomizing base 30 is mounted in the atomizing base mounting slot 1214, and one end surface of the atomizing base 30 resists the resisting wall 1218. Two electrode mounting holes are defined on the atomizing base 30, and both electrode mounting holes communicate with the atomizing core mounting slot 1216. Thus, the electrode 32 can be accommodated in the electrode mounting holes and electrically connected to the atomizing core 40.

Additionally, the atomizing base 30 is further provided with at least one connecting hole 34 between the two electrode mounting holes, and the connecting hole 34 communicates with the atomizing core mounting slot 1216 to collectively form an air inlet passage communicating with the atomizing chamber. Thus, air flow outside the liquid storage bottom wall 121 may enter the atomizing chamber through the air inlet passage.

In one of embodiments, the outer surface of the liquid storage side wall 123 away from the liquid storage chamber 125 has an air inlet groove 1232 extending to the liquid storage bottom wall 121. One end of the air inlet groove 1232 communicates with the external environment through the nozzle cover 14 and the other end of the air inlet groove 1232 communicates with the atomizing chamber through an air inlet passage formed in the liquid storage bottom wall 121. In this way, when the user sucks the electronic cigarette 300, the external air may enter the air inlet groove 1232 through the nozzle cover 14, and then may enter the side of the liquid storage bottom wall 121 along the air inlet groove 1232, then enters the atomizing core 40 through the air inlet passage defined on the liquid storage bottom wall 121. In contrast to the prior art where external air adjacent to the liquid storage bottom wall 121 enters the atomizing core 40 through the liquid storage bottom wall 121, the provision of the air inlet groove 1232 obviously extends the air flow path, thereby reducing the sound generated by the flowing airflow (the shorter the airflow flow path, the greater the sound of the airflow), optimizing the usage experience of the electronic cigarette 300.

Particularly, in one of the embodiments, the liquid storage side wall 123 is provided with two sets of air inlet grooves 1232, which are respectively provided on opposite sides of the liquid storage side wall 123, each set of air inlet grooves 1232 includes one or more air inlet grooves 1232, each air inlet groove 1232 extends linearly from the middle of the liquid storage side wall 123 along the central axis of the liquid storage chamber 125 to the liquid storage bottom wall 121. Thus, a plurality of airflow flows smoothly in a straight line into the liquid storage bottom wall 121, and the air intake efficiency is high.

Particularly, in one of the embodiments, the liquid storage side wall 123 includes two first sidewalls spaced apart in the width direction of the liquid storage cartridge 12 and two second sidewalls spaced and symmetrically provided in the length direction of the liquid storage cartridge 12. Two side edges of the second side wall in the width direction of the liquid storage cartridge 12 connect the two first side walls, respectively. One set of air inlet grooves 1232 includes only one air inlet groove 1232 provided at the junction of one first side wall and the first and second side wall, and the other set of air inlet grooves 1232 includes two air inlet grooves 1232 respectively provided at two connections between one second side wall and two first side walls, and the two air inlet grooves 1232 communicate with each other. It should be understood that, in alternative embodiments, the number, shape, and opening position of the air inlet groove 1232 are not limited thereto, and may be provided as needed.

Referring to FIG. 2 and FIG. 3, the nozzle cover 14 is detachably mounted on the open end of the liquid storage cartridge 12, and includes a nozzle cover top wall 141 and a nozzle cover side wall 143. The nozzle cover side wall 143 extends in the same direction from the edge of the nozzle cover top wall 141. The nozzle cover side wall 143 surrounds the nozzle cover top wall 141 and forms an open mouth cavity at one end with the nozzle cover top wall 141, The open end of the liquid storage cartridge 12 is inserted into the nozzle cavity so as to pass through the liquid storage chamber 125 sealed by the nozzle cover 14.

Two air outlet holes 1412 are provided at intervals on the nozzle cover top wall 141. The air outlet holes 1412 communicate with the vent tube 50, and smoke in the vent tube 50 is discharged through the air outlet holes 1412 to be inhaled by the user. It should be understood that in alternative embodiments, the number and size of the air outlet holes 1412 are not limited and may be provided as desired.

One end of the nozzle cover side wall 143 away from the nozzle cover top wall 141 is provided with an air inlet hole 1432 corresponding to the end of the air inlet groove 1232 on the liquid storage side wall 123. An end of the air inlet groove 1232 away from the liquid storage bottom wall 121 communicates with the external environment through the air inlet hole 1432, Thus, when the user inhales the electronic cigarette 300, the external air enters the air inlet groove 1232 through the air inlet hole 1432 on the nozzle cover 14.

Additionally, a buckle 1234 is protruded from an outer surface of the liquid storage side wall 123 with an air inlet groove 1232. When the nozzle cover 14 is covered on the liquid storage cartridge 12, the buckle 1234 is latched in the air inlet hole 1432 in the nozzle cover side wall 143. In this way, the air inlet hole 1432 integrates the function of latching and air inletting, so as to allow the external air into the air inlet groove 1232, and the nozzle cover 14 can be firmly fixed to the liquid storage cartridge 12.

It can be understood that in alternative embodiments, the liquid storage side wall 123 may be provided with no air inlet groove 1232, and the nozzle cover side wall 143 may be provided with no air inlet hole 1432. The external air directly enters the air inlet passage of the liquid storage bottom wall 121 through an opening in the power supply device 200.

One end of the vent tube 50 is connected to the atomizing core housing 41, and the other end of the vent tube 50 extends to the open end of the liquid storage cartridge 12 and communicates with the air outlet holes 1412 of the suction nozzle cap top wall 141. Thus, the smoke generated by heating the atomizing liquid by the atomizing core 40 is conveyed to the open end of the liquid storage cartridge 12 through the vent tube 50.

In some of the embodiments, the vent tube 50 is integrally formed with the atomizing core housing 41, so that no extra component for fixing the atomizing core 40 and the vent tube 50 is required, further simplifying the structure of the atomizing device 100 and improving the sealing performance.

In some of the embodiments, the atomizing device 100 also includes a gasket 60. The gasket 60 is mounted at the open end of the liquid storage cartridge 12 and is interference-fitted with the liquid storage cartridge 12, the nozzle cover 14 applies pressure to the gasket 60 in a direction toward the liquid storage bottom wall 121, and one end of the vent tube 50 away from the atomizing core 40 is inserted into the gasket 60. Thus, the gasket 60 and the nozzle cover 14 cooperatively seal the open end of the liquid storage chamber 125, thereby preventing the leakage of the atomizing liquid in the liquid storage chamber 125.

In the atomizing device 100, since two or more liquid injection channels 1212 are provided, the air in the liquid storage chamber 125 can be discharged simultaneously during injecting the atomizing liquid, so that the atomizing liquid effectively fills the liquid storage chamber 125, preventing the leakage of the atomizing liquid in the atomizing core 40 under the effect of the internal and external pressure difference. Also, the sealing plug inserted in the injection channel 1212 is magnetically engaged with the power supply device 200, so as to prevent being fail due to the wear of the long-term contact. At the same time, no other connecting structure is needed to connect the sealing plug 20 and the power supply device 200, thus simplifying the structure of the atomizing device 100. Further, since the liquid injection channel 1212 is opened in the liquid storage bottom wall 121 mounted with the atomizing core 40, the atomizing liquid does not contact with the atomizing core 40 during the liquid injection process, thereby eliminating the restriction on the liquid injection time, and preventing the atomizing liquid from flowing out of the atomizing core 40 during the injection process. Further, since the atomizing core 40 is provided integrally with the vent tube 50, fixing parts are reduced, and the internal structure of the atomizing device 100 is simplified. Since the atomizing base 30 is independent of the liquid storage chamber 125 and is not in contact with the atomizing liquid, the problems of liquid leakage and liquid infiltration on the side of the bottom cover of the atomizing device 100 in the prior art are solved. In addition, since the atomizing device 100 uses the connection part of the nozzle cover 14 and the liquid storage cartridge 12 for air inlet, the flow length of the air flow is prolonged, thereby reducing the sound of the air flow generated during the operation of the atomizing device 100 and improving the user experience.

The technical features of the embodiments described above can be arbitrarily combined. In order to make the description succinct, there is no describing of all possible combinations of the various technical features in the foregoing embodiments. It should be noted that there is no contradiction in the combination of these technical features which should be considered as the scope of the description.

Although the present disclosure is illustrated and described herein with reference to specific embodiments, the present disclosure is not intended to be limited to the details shown. It is to be noted that, various modifications may be made in the details within the scope and range of equivalents of the claims and without departing from the present disclosure. Therefore, the protection scope of the present disclosure shall be subject to the protection scope of the claims.

What is claimed is:

1. An atomizing device, comprising:
a liquid storage housing provided with a liquid storage chamber and a liquid injection channel, wherein the liquid storage chamber is in fluid communication with an external environment via the liquid injection channel; and
a sealing plug detachably inserted into the liquid injection channel to open or seal the liquid storage chamber, wherein when the sealing plug is inserted into the liquid injection channel, the sealing plug seals the liquid storage chamber, wherein when the sealing plug is removed from the liquid injection channel, the liquid storage chamber is configured to be open to the external environment via the liquid injection channel, wherein the sealing plug has a first end facing toward the liquid storage chamber and a second end opposite the first end and facing away from the liquid storage chamber,
wherein the second end of the sealing plug is provided with a magnetic attraction surface having magnetism.

2. The atomizing device of claim 1, wherein the sealing plug is made of a magnet or a magnetic material that generates a magnetic attraction with a magnet.

3. The atomizing device of claim 1, wherein the liquid storage housing is provided with at least two liquid injection channels, and each of the liquid injection channels is detachably mounted with the sealing plug.

4. The atomizing device of claim 1, wherein the liquid storage housing comprises a liquid storage cartridge, the liquid storage cartridge comprises a liquid storage bottom wall and a liquid storage side wall extending in the same direction from an edge of the liquid storage bottom wall, the liquid storage side wall surrounds the liquid storage bottom wall and the liquid storage side wall and the liquid storage bottom wall cooperatively form the liquid storage chamber with one end open, and the liquid injection channel is provided at the liquid storage bottom wall.

5. The atomizing device of claim 4, wherein the liquid storage housing further comprises a nozzle cover detachably provided at the open end of the liquid storage housing to seal the liquid storage chamber.

6. The atomizing device of claim 4, further comprising an atomizing core, wherein a side of the liquid storage bottom wall adjacent to the liquid storage chamber is provided with a mounting slot in communication with the liquid storage chamber, an end of the atomizing core is inserted into the mounting slot, and the other end of the atomizing core is located in the liquid storage chamber.

7. The atomizing device of claim 6, further comprising a vent tube, wherein an end of the vent tube is connected to the atomizing core, and the other end of the vent tube extends to the open end of the liquid storage cartridge, and the atomizing core comprises an atomizing core housing and an atomizing core body accommodated in the atomizing core housing, the atomizing core housing is integrally formed with the vent pipe.

8. The atomizing device of claim 7, further comprising a sealing gasket mounted on the open end of the liquid storage cartridge, wherein the end of the vent tube away from the atomizing core is inserted into the sealing gasket.

9. The atomizing device of claim 4, further comprising an atomizing base, wherein a side of the liquid storage bottom wall away from the liquid storage chamber is provided with a mounting slot, and the atomizing base is mounted in the mounting slot.

10. The atomizing device of claim 1, wherein the second end of the sealing plug is exposed to the external environment, and wherein the magnetic attraction surface of the second end is configured to magnetically couple to a magnetic element of a power supply device when the sealing plug is inserted into the liquid injection channel.

11. The atomizing device of claim 1, further comprising a top wall and a bottom wall, wherein at least one air outlet hole is provided on the top wall and is configured to communicate with a vent tube for smoke discharge, and wherein when the sealing plug is inserted into the liquid injection channel, the second end is exposed through an opening in the bottom wall.

12. An electronic cigarette, comprising:
an atomizing device comprising:
a liquid storage housing provided with a liquid storage chamber and a liquid injection channel, wherein the liquid storage chamber is in fluid communication with an external environment via the liquid injection channel; and
a sealing plug removably and detachably inserted into the liquid injection channel to open or seal the liquid storage chamber, wherein the sealing plug has a first end facing toward the liquid storage chamber and a second end opposite the first end and facing away from the liquid storage chamber, wherein the second end of the sealing plug is provided with a magnetic attraction surface having magnetism; and
a power supply device provided with a magnetic element, wherein the magnetic element and the magnetic attraction surface are connected to each other under a magnetic attraction, such that the atomizing device is coupled to the power supply device.

13. The electronic cigarette of claim 12, wherein the atomizing device further comprises a top wall and a bottom wall, wherein at least one air outlet hole for smoke discharge is provided on the top wall, and wherein when the sealing plug is inserted into the liquid injection channel, the second end is exposed through an opening in the bottom wall.

* * * * *